United States Patent [19]

Finney

[11] Patent Number: 4,549,530
[45] Date of Patent: Oct. 29, 1985

[54] MALE URINARY INCONTINENCE DEVICE AND METHOD

[75] Inventor: Roy P. Finney, Tampa, Fla.

[73] Assignee: Medical Engineering Corporation, Racine, Wis.

[21] Appl. No.: 527,291

[22] Filed: Aug. 29, 1983

[51] Int. Cl.⁴ ............................ A61B 19/00; A61F 1/00
[52] U.S. Cl. .................................... 128/1 R; 128/79; 128/DIG. 25
[58] Field of Search .......... 128/1 R, 79, 346, DIG. 25

[56] References Cited

U.S. PATENT DOCUMENTS

| | | | |
|---|---|---|---|
| 2,455,859 | 12/1948 | Foley | 128/346 |
| 2,533,924 | 12/1950 | Foley | 128/346 |
| 3,203,421 | 8/1965 | Bialick | 128/346 |
| 3,854,469 | 12/1974 | Giori et al. | 128/1 R |
| 3,863,622 | 2/1975 | Buuck | 128/1 R |
| 3,903,894 | 9/1975 | Rosen et al. | 128/346 |
| 3,939,821 | 2/1976 | Roth | 128/1 R |
| 4,019,499 | 4/1977 | Fitzgerald | 128/1 R |
| 4,428,365 | 1/1984 | Hakky | 128/1 R |

*Primary Examiner*—Dalton L. Truluck
*Attorney, Agent, or Firm*—Quarles & Brady

[57] ABSTRACT

A method of controlling urinary incontinence in a male comprises implanting in the penis of the male a relatively rigid backup support against which the urethra can be collapsed, anchoring said backup support to prevent it from migrating, and exerting pressure upon only one side of the urethra to collapse and keep it closed against the backup support. The preferred backup support includes a groove which receives the neurovascular bundle and protects the major blood and nerve supplies of the penis from the adverse effects of pressure exerted on the urethra. Devices for practicing the method are also disclosed.

10 Claims, 10 Drawing Figures

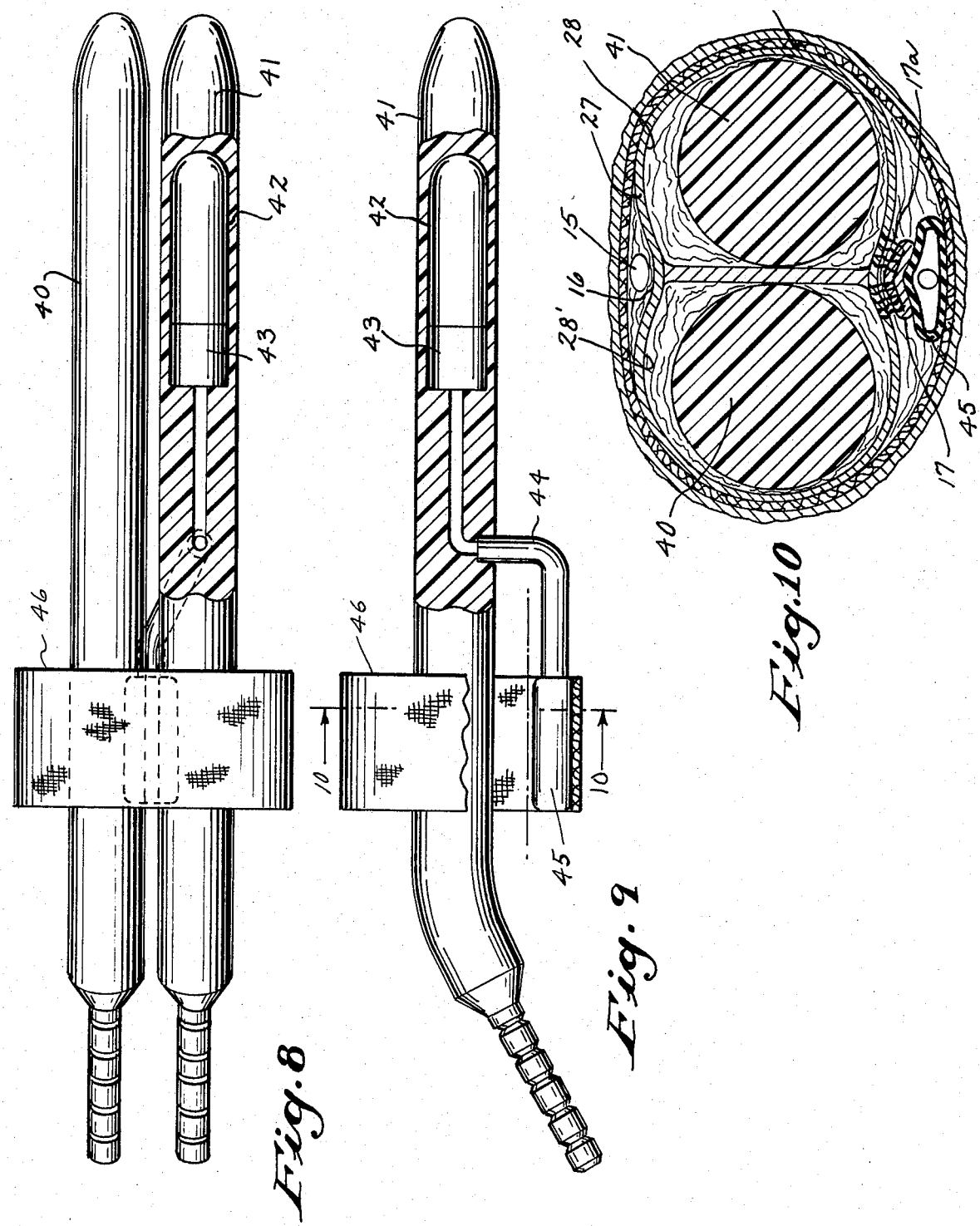

MALE URINARY INCONTINENCE DEVICE AND METHOD

FIELD OF THE INVENTION

The present invention relates to a novel method of controlling male incontinence and improved devices for practicing that method.

BACKGROUND OF THE INVENTION

Many men have non-functioning or malfunctioning urethral sphincters because of congenital malformations, trauma to the sphincter nerves or muscles, or disease of the sphincter nerves or muscles. A properly functioning urethral sphincter retains urine in the bladder until the sphincter is voluntarily relaxed which permits the urine to be discharged. When the urethral sphincter fails to function properly, uncontrolled drainage of urine from the bladder can occur. Obviously, this can be embarrassing to the individual and it can restrict his activities.

Numerous attempts have been made in the past to provide an artificial sphincter which can serve as a substitute for a malfunctioning urethral sphincter. Two such devices have enjoyed some commercial success. The first, the Rosen Inflatable Urinary Incontinence Prosthesis is described in Rosen et al U.S. Pat. No. 3,903,894, and the second, a more complex hydraulic device, is described in the Buuck et al. U.S. Pat. No. 3,863,622. The use of both of these devices has not been without problems and their acceptance has been limited.

There also have been attempts made to use simpler, less complex, external penile clamps to control male incontinence. Representative of such devices are the so-called Cunningham clamp which has been available since the 1920's and the devices shown in Foley U.S. Pat. Nos. 2,455,859 and 2,533,924. The primary disadvantage of the external penile clamps is that they cut off the major blood and nerve supplies to the penis and interfere with lymphatic drainage. As a result, congestion, edema, pain, inflammation and tissue erosion of the penis can result.

SUMMARY OF THE INVENTION

It is the primary object of the present invention to provide a novel, simple, and effective method of controlling male incontinence and devices for use in that method.

It is a further object to disclose a method and devices for controlling male incontinence which do not cut off the major blood and nerve supplies to the penis and do not interfere with lymphatic drainage so that congestion, edema, inflammation, pain, and tissue erosion of the penis are avoided.

It is a still further object to disclose a method and devices for collapsing the urethra to prevent urine flow without causing necrosis of the urethra.

The novel method of the present invention for controlling male urinary incontinence comprises implanting into the patient's penis a backup support means of biocompatible material against which the urethra can be collapsed, anchoring said means to prevent it from migrating and selectively exerting pressure on only one side of the urethra to collapse it and keep it closed against the backup support means. The urethra is opened to permit urine flow from the bladder by the patient relieving the pressure exerted on the urethra.

The preferred incontinence devices for use in the practice of the method of the present invention include a backup support means comprising a pair of relatively rigid members of biocompatible material which are sized and shaped for implanting in the corpora cavernosum of the penis, means for anchoring the relatively rigid members in place to prevent them from migrating out of position and means operable by the user for selectively applying pressure on only one side of the urethra to collapse it and hold it in a closed position against the backup support means. The preferred backup means also protects the neurovascular bundle, which contains the major blood, nerve and lymphatic supplies of the penis, from the adverse effects of the pressure applied upon the urethra to keep it closed.

The above and further objects of the invention will be apparent from the description and drawings which follow.

BRIEF DESCRIPTION OF THE DRAWINGS

The invention will be hereinafter more fully described with reference to the accompanying drawings in which:

FIG. 8 is a top view, partly in section, showing another embodiment in which the backup support means is a pair of rod shaped penile implants;

FIG. 9 is a side view of the embodiment of FIG. 9; and

FIG. 10 is a cross-sectional view of a penis in which the embodiment of FIG. 8 has been implanted.

DESCRIPTION OF THE PREFERRED EMBODIMENT

Figure 1:
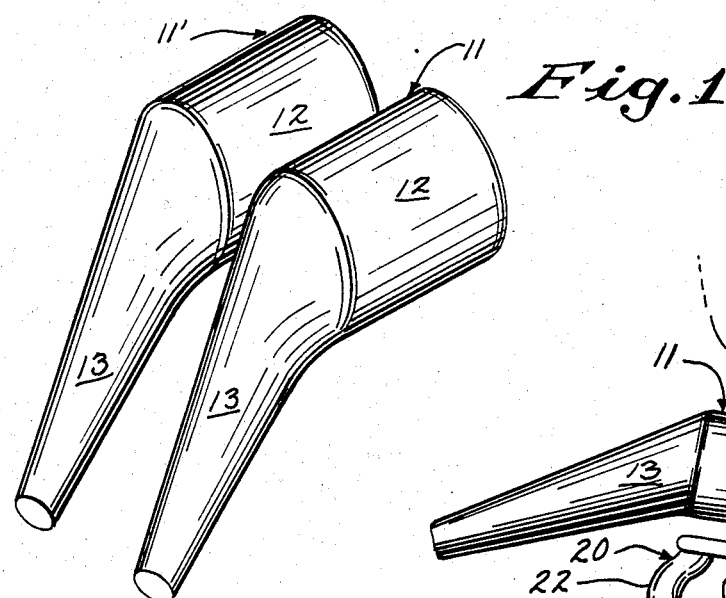
FIG. 1 is a perspective view of the preferred embodiment of the backup support means of the present invention.

One embodiment of the backup support means of the present invention is seen in FIG. 1. As seen therein the backup support means includes a pair of identical relatively rigid members 11, 11' each having a relatively short cylindrical main body 12, 12' and a proximal stem 13, 13' which can be used to anchor the member in position in the corpora cavernosum of a penis. The members 11, 11' are formed of a biocompatible material of sufficient rigidity for the intended use and all of the sides and the edges of the members are round and smooth to minimize tissue damage.

As seen in FIGS. 2 to 7 of the drawings, the main body 12 of the relatively rigid member 11 is implanted in one of the corpora cavernosum of a human penis 14 with the stem 13 in the crus of the corporus and main body 12 positioned near the base of the penile shaft. When both of the relatively rigid members 11, 11' are thus positioned, the neurovascular bundle 15 containing the major nerve, blood and lymphatic supplies for the penis is positioned above a groove 16 created by the crests of the members 11, 11' and the urethra 17 is positioned below a second groove 18 created by the bottoms of the members 11, 11'.

Figure 6:
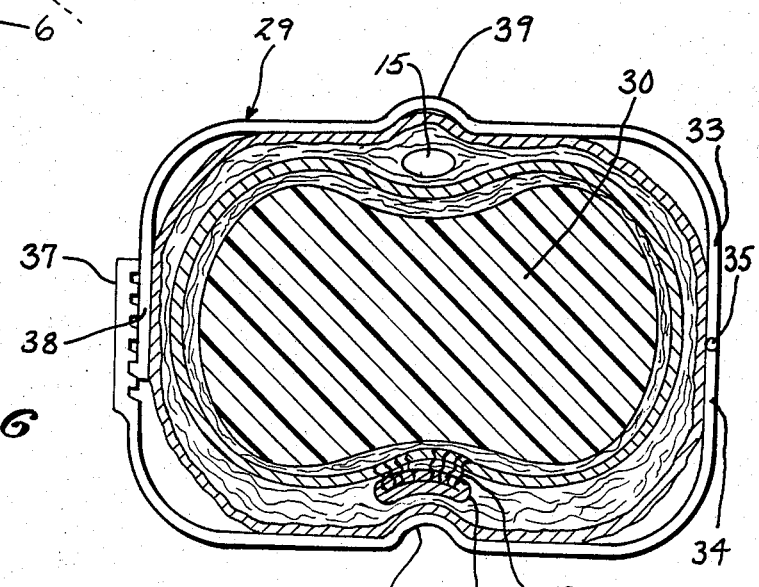
FIG. 6 is a sectional view taken along lines 5—5 in FIG. 5 and showing the urethra closed.
Figure 7:
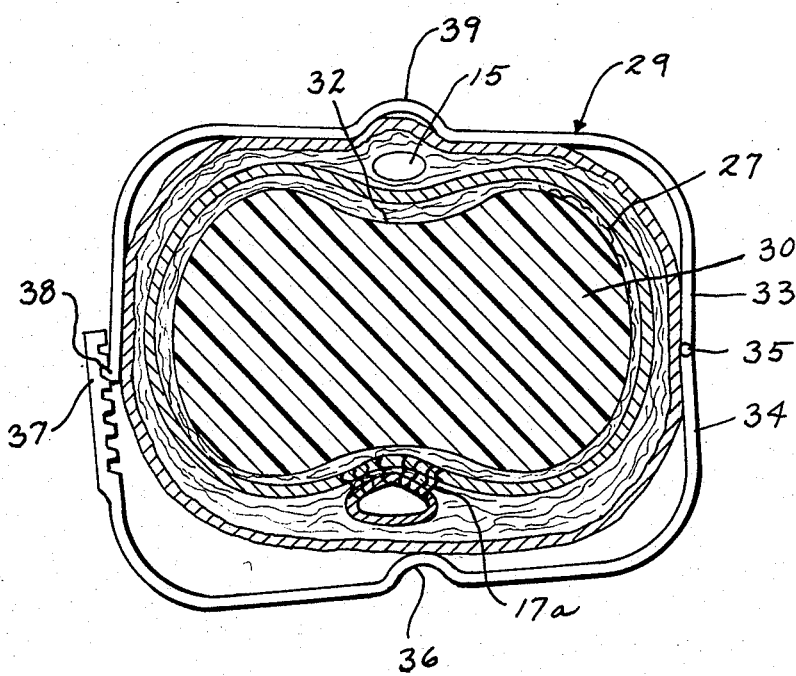
FIG. 7 is a view similar to FIG. 6 with the urethra open.

Although the backup support means just described is in the form of a pair of members 11, 11' the main bodies of two members could be made in the form of a single piece such as the member 19 seen in FIGS. 6 and 7. The backup support means may also be a pair of penile implants of the type shown in the Finney et al. U.S. Pat. No. 4,066,073, or an inflatable penile implant which provides sufficient support to serve as an effective backup support means. A particularly preferred type of penile implant for this use is seen in FIGS. 8, 9 and 10. The use of the rod-shaped penile implants is indicated when the patient wishes to retain the ability to have an erection after surgery.

Figure 2:
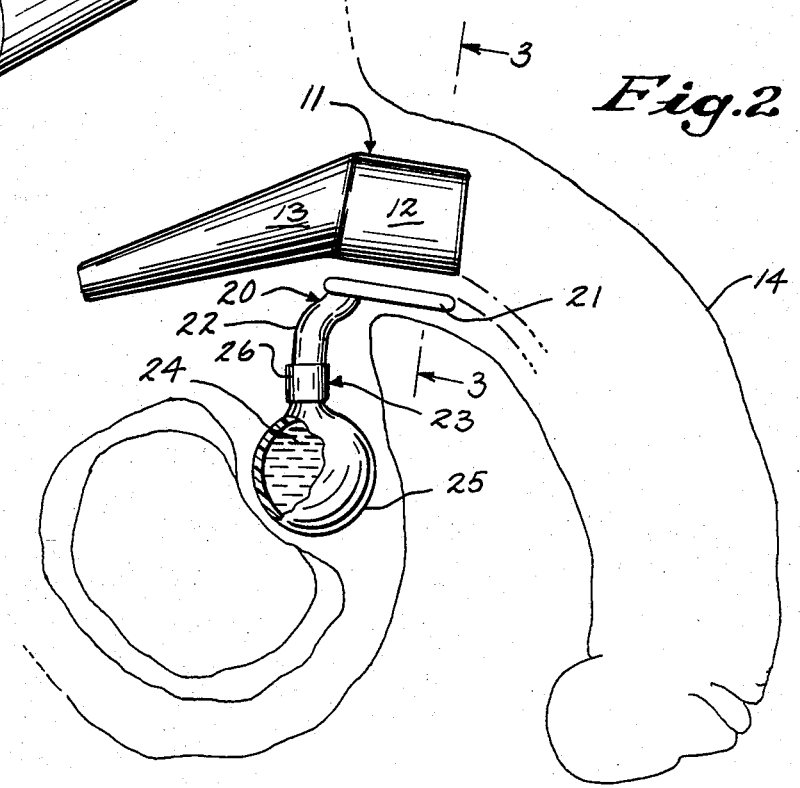
FIG. 2 is a view, partly in section, showing the backup support means of FIG. 1 and a pressurizing means for selectively exerting pressure on the urethra implanted in a male.
Figure 3:
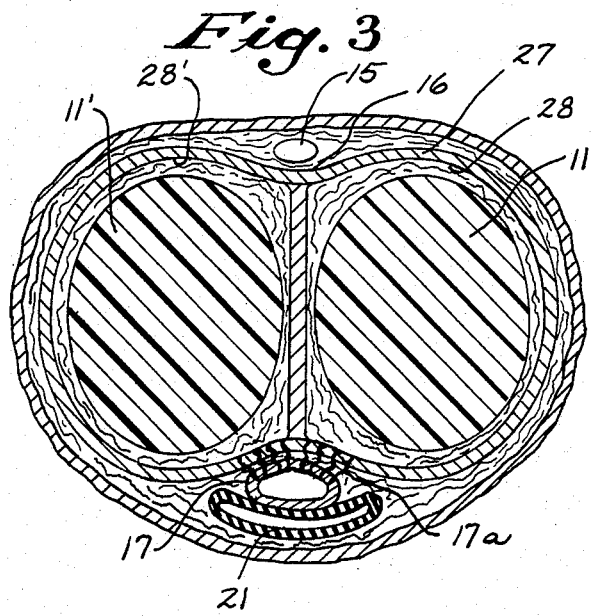
FIG. 3 is a sectional view taken along lines 3—3 in FIG. 2 and showing the urethra open.
Figure 4:
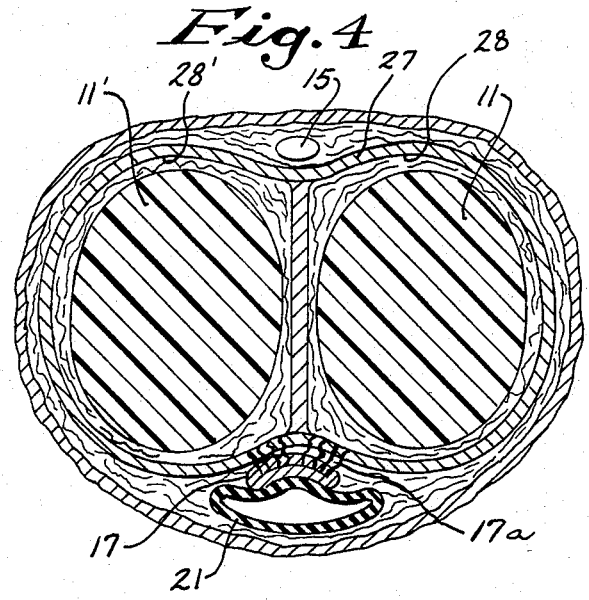
FIG. 4 is a view similar to FIG. 3 with the urethra closed.

The embodiment of the invention shown in FIGS. 2 to 4 includes an implanted pressurizing means, generally referred to as 20. As seen therein, the pressurizing means 20 includes an inflatable balloon 21 which is implanted directly below the urethra 17 and the groove 18. The balloon 21 may be provided with a nonextensible reinforced back that can be sutured to tissue to anchor it in place or anchored in place with a belt which encircles the penile shaft as seen in the embodiment of FIGS. 8, 9 and 10. The balloon 21 is connected by tubing 22 to a pump assembly 23 which contains pressurizing fluid 24. The pump assembly 23 which is positioned in the scrotum of the patient consists of a pressure bulb 25 and a suitable control valve 26. The control valve 26 is a pressure regulating value of the type which opens when the bulb 25 is squeezed and closes when it is released. The valve 26 can be manually opened by the patient from the outside so that the balloon 21 can be deflated to permit the bladder to empty through the open urethra 17.

The preferred control valve 26 also opens automatically to prevent excess pressure from being exerted on the urethra 17. Excessive pressure could obstruct the blood supply 17a to the urethra and cause ischemia which in turn will cause necrosis in the urethra at the point of pressure. A suitable valve 26 which can be manually opened and which automatically opens when the pressure in the balloon exceeds a predetermined level is described in U.S. Pat. No. 4,167,952.

As shown, only in FIG. 4, the balloon 21, when it is inflated with pressurizing fluid 24, selectively expands and applies pressure upon only one side of the urethra 17 causing it to collapse against the tunica albugina 27 which surrounds the corpora cavernosum 28, 28'. The tunica albugina 27 is supported by the relatively rigid members 11 and 11'. When the urethra 17 is collapsed no urine can flow therethrough. When urination is desired, the valve 26 is manually opened by the patient to permit the pressurizing fluid 24 to flow back to the bulb 25 and the balloon 21 deflates. The urethra 17 then opens as a result of the fluid pressure in the bladder (not shown).

Still referring to FIG. 4 it can be seen that the compressive pressure which is applied by the balloon 21 to collapse the urethra 17 does not adversely affect the major blood, nerve and lymphatic supplies in the neurovascular bundle 15. The pressure applied to the urethra 17 is transferred to the tunica albugina 27 and in turn to the crests 11a and 11'a on the top of the relatively rigid members 11 and 11'. The neurovascular bundle 15 which is in the groove 16 is protected from the pressure. As a result, the penis continues to have an adequate blood, nerve and lymphatic supply and congestion, edema, pain, inflammation and tissue erosion are prevented. The use of the balloon 21 which applies pressure to only one side of the urethra 17 does not cut off the blood supply 17a to the urethra as does the use of the prior art urethra encircling cuffs. Even when the urethra 17 is collapsed sufficient blood is able to reach the urethra via the blood supply 17a to prevent necrosis.

Figure 5:
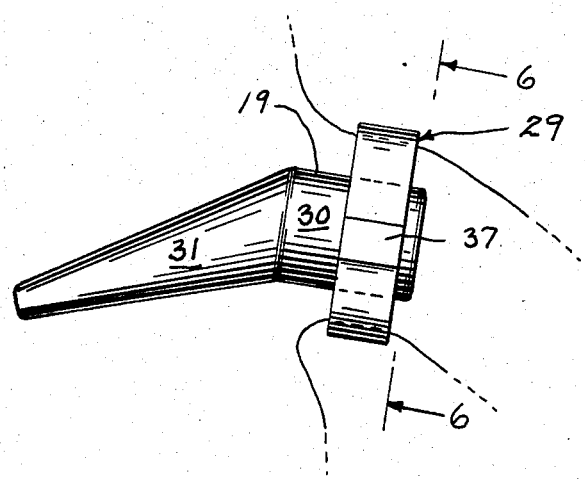
FIG. 5 is a view, partly in section, showing a backup support means similar to that of FIG. 1 implanted in a penis and an external clamp positioned to exert selective pressure on the urethra.

In the embodiment seen in FIGS. 5 to 7, an externally located pressurizing means or clamp 29 is used with an implanted backup support means 19. The backup support means is similar to that of FIG. 1 except that there is a single unitary main body 30 with a pair of identical anchoring stems 31 of which only one can be seen in FIG. 5. When such a unitary main body is employed, the septum separating the corpora is removed.

In the practice of the present invention, the clamp 29 is not used by itself to accomplish urinary control; it is used only in conjunction and in cooperation with the backup support means which protects the major blood, nerve and lymphatic supplies of the penis from the adverse effects of pressure exerted on the urethra. The clamps of the prior art which were used by themselves squeezed and compressed all the soft tissue of the flaccid penis including the major blood, nerve and lymphatic supplies and their use invariably resulted in complications such as congestion, inflammation, edema or pain. As seen best in FIG. 6, the clamp 29 can be used without causing such complications because even when the clamp 29 is closed and the urethra 17 is collapsed against the backup support means 19, the neurovascular bundle 15 is in the top groove 32 and protected from destructive pressure.

In the preferred embodiment shown in FIGS. 5 to 7, the clamp 29 is made up of a top half 33 and a bottom half 34 joined by a hinge 35. The inside of the bottom half 34 of the clamp 29 has an inwardly directed protuberance or dome 36 which when the clamp is closed applies selective pressure on only one side of the urethra 17 causing it to collapse against the backup support means 19 as seen in FIG. 6. Although a simple hook 37 and catch 38 type of fastening means for the clamp is shown in the drawings, it will be appreciated that other forms of releasable fasteners can be used.

The clamp 29 also has an outwardly extending dome 39 on the inside of the top half 33 which further insures that the neurovascular bundle 15 will not be subjected to excessive pressure with undesired results. The clamp 29 is normally closed, but can be opened as seen in FIG. 7 to permit urination.

It will be appreciated by those skilled in the art that the external pressurizing means 29 may take other forms than a clamp; for example, it might be a belt with a properly positioned inwardly directed protuberance which would function like the dome 36 to selectively collapse the urethra. The external pressuring means may be made of a wide variety of materials having suitable properties.

In FIGS. 8, 9 and 10, still another embodiment of the invention is shown. In this embodiment the backup support means is a pair of rod-type penile implants. One of the pair of implants 40 is a conventional rod-type penile implant. The other penile implant 41 is a rod-type implant which includes a pump reservoir 42 and a pressure regulatory control valve 43 and it is connected by tubing 44 to an inflatable balloon 45. The pump reservoir 42 has resilient walls and it contains pressurizing fluid for pressurizing the balloon 45 which is positioned opposite the urethra 17 as shown in FIG. 10. As seen in FIGS. 8, 9 and 10, the balloon 45 is affixed to an anchoring belt 46 for encircling the penile shaft under the penile skin. The use of the anchoring belt 46 is optional and other means of positioning and anchoring the balloon 44 can be used.

The balloon 44 is normally pressurized keeping the urethra 17 collapsed as seen in FIG. 10. In this state, the balloon 45 is kept pressurized at a desired safe pressure by the pressure regulating control valve 43 and the reservoir of the pump reservoir 42 is partly empty. When the patient desires to urinate the pressure regulating control valve 45 is manually squeezed to allow the pump reservoir 42 to suck pressurizing fluid out of the balloon 45 and into the reservoir. As the balloon 45 deflates fluid pressure in the bladder opens the urethra and urination occurs. A suitable pump reservoir for use in this embodiment is that shown in U.S. Pat. No. 4,167,952.

Medical grade silicone rubber is the preferred material for the backup support means because it is biocompatible and it can be formulated to provide a material which possesses suitable tensile strength, rigidity and softness for the intended function. However, other materials, such as polyurethane, which possess the desired properties also may be used. In order to minimize the possibility of erosion through the penile skin, the backup support means is preferably covered with a soft layer of material and all edges are arced or curved to minimize tissue damage.

All components to be implanted, including the belt 46 and the balloons 21 and 45, are made of a biocompatible material. Especially preferred for these components is a mesh reinforced silicone elastomer which does not expand or in the case of the balloons, expands only to a limited predetermined extent and only in the desired direction.

The preferred method of implanting the backup support means is through the perineum. After making an appropriate incision, the corpora cavernosum are dilated distally and proximally to accept the relatively rigid members 11 and 11'. The appropriate anatomical measurements are made to insure that the stems of the members are in the crus of the corpora. The main body members are then positioned in the corpora near the base of the penile shaft as shown in FIG. 2. When the members 11 and 11' are properly positioned, the neurovascular bundle 15 is located in the top groove formed by the crests of two members 11 and 11' and the urethra 17 is opposite the bottom groove 18. If an external pressurizing means is to be used, the incision may then be closed. If an implantable pressurizing means such as that of FIGS. 2 to 4 is to be used, the balloon 21 will be first properly positioned and anchored opposite the urethra 17 and the pump assembly will be placed in the scrotum before the necessary incisions are closed.

When the backup support means takes the form of two rod shaped penile implants as seen in FIGS. 8, 9 and 10, the implants are positioned and anchored in the corpora cavernosum in conventional manner and the neurovascular bundle 15 is located in the groove-like recess formed by the crests of the two implants 40 and 41. When thus positioned, the blood, nerve and lymphatic supplies are protected from the pressure exerted on the urethra. When the implant 41 is employed, the balloon 45 is positioned opposite the urethra 17 and the optional belt 46 is positioned about the penile shaft beneath the skin before the incision is closed.

The novel method and devices of the present invention are a significant advancement over prior art devices because they protect the neurovascular bundle from the adverse effects of pressure. They also are superior to prior art devices because the balloon exerts pressure upon only one side of the urethra thus permitting the urethra tissue to receive an adequate blood supply even when the urethra is collapsed.

It is to be understood that the foregoing description and drawings are for purposes of illustration and that a number of modifications and changes may be made without departing from the spirit and scope of the present invention. Therefore, the invention is not to be limited by any of the specific embodiments described but only by the claims which follow:

I claim:

1. A method of controlling urinary incontinence in a male patient which comprises implanting into the corpora cavernosum of the patient's penis relatively rigid backup support means of biocompatible material against which the urethra can be collapsed, anchoring said means to prevent it from migrating and then exerting selective pressure upon only one side of the urethra to collapse it and keep it closed against the backup support means.

2. The method of claim 1 in which the selective pressure is exerted upon only one side of the uretha by a balloon implanted in the penis which is inflated by an implanted pump.

3. The method of claim 1 in which the selective pressure is exerted upon only one side of the urethra by an external clamp.

4. A urinary incontinence device for a male patient comprising relatively rigid backup support means of biocompatible material for implanting in the corpora cavernosum of the penis of the patient to provide a support against which the patient's urethra can be collapsed, anchoring means for keeping said backup support means properly positioned in the penis, pressurizing means for selectively exerting pressure upon only one side of the urethra to collapse it and keep it closed against the backup support means and means for relieving the pressure exerted by the pressurizing means so that the urethra will open to permit fluid flow.

5. A device of claim 4 in which the backup support means is a pair of rod-like members, each of said members having a cylindrical main body and an integral stem.

6. A device of claim 4 in which the pressurizing means for selectively exerting pressure upon only one side of the urethra includes an inflatable balloon, pump means for inflating the balloon with pressurizing fluid to cause it to expand to exert selective pressure against one side of the urethra, and valve means for controlling the flow of pressurizing fluid between the pump and the balloon and controlling the pressure in the balloon at a safe level.

7. A device of claim 4 in which the pump is a pressure bulb.

8. A device of claim 4 in which the pressurizing means for selectively exerting pressure upon one side of the urethra is an external clamp.

9. A device of claim 4 in which the backup support means consists of a pair of rod-shaped penile implants adapted to be implanted in the corpora cavernosum.

10. A device of claim 9 in which the pressurizing means is a balloon and a pump reservoir in one of the implants, said pump reservoir being connected by tubing to the balloon.

* * * * *